(12) United States Patent
Nobis et al.

(10) Patent No.: US 7,789,825 B2
(45) Date of Patent: Sep. 7, 2010

(54) HANDLE FOR ENDOSCOPIC DEVICE

(75) Inventors: Rudolph Nobis, Mason, OH (US);
Christopher J. Hess, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 10/674,186

(22) Filed: Sep. 29, 2003

(65) Prior Publication Data
US 2005/0070764 A1 Mar. 31, 2005

(51) Int. Cl.
*A61B 1/00* (2006.01)

(52) U.S. Cl. ............... 600/131; 600/104; 600/118; 600/153; 600/154; 606/1; 606/170; 606/205

(58) Field of Classification Search .......... 600/131; 604/1, 170, 205
See application file for complete search history.

(56) References Cited

U.S. PATENT DOCUMENTS

| | | | |
|---|---|---|---|
| 3,643,653 A * | 2/1972 | Takahashi et al. ......... 600/129 |
| 4,655,219 A | 4/1987 | Petruzzi |
| 4,909,789 A | 3/1990 | Akihiro et al. |
| 5,152,278 A * | 10/1992 | Clayman ................ 600/131 |
| 5,352,235 A | 10/1994 | Koros et al. |
| 5,431,675 A | 7/1995 | Nicholas et al. |
| 5,483,952 A | 1/1996 | Aranyi |
| 5,562,655 A | 10/1996 | Mittelstadt et al. |
| 5,624,379 A * | 4/1997 | Ganz et al. .............. 600/104 |
| 5,626,597 A | 5/1997 | Urban et al. |
| 5,741,286 A | 4/1998 | Recuset |
| 5,810,876 A | 9/1998 | Kelleher |
| 5,827,323 A | 10/1998 | Klieman et al. |
| 5,830,231 A | 11/1998 | Geiges, Jr. |
| 5,908,436 A | 6/1999 | Frank et al. |
| 5,951,575 A | 9/1999 | Bolduc et al. |
| 6,162,209 A | 12/2000 | Gobron et al. |

(Continued)

FOREIGN PATENT DOCUMENTS

DE    203 11 293 U1    9/2003

(Continued)

OTHER PUBLICATIONS

EPO Search Report dated Dec. 28, 2004 for corresponding patent application, European Patent Application No. EP 04 25 6001.

(Continued)

*Primary Examiner*—Matthew J Kasztejna

(57) ABSTRACT

An endoscopic accessory medical device is provided. The device can include a handle, a flexible shaft, and an end effector. The handle can include an actuator for operating the end effector through a wire or cable pulling member that extends through the flexible shaft. The handle and actuator can be operable with a single hand, such that the operation of the end effector can be accomplished with the same hand that is used to hold the handle and advance the end effector through an endoscope. The handle can include an actuation mechanism that is decoupled from operation of the end effector when the actuator is in a first open position, which becomes operatively coupled to the end effector when the actuator is moved to a second position, such as by squeezing the actuator, and which operates the end effector when the actuator is moved further to a third position.

9 Claims, 14 Drawing Sheets

U.S. PATENT DOCUMENTS

| | | | |
|---|---|---|---|
| 6,299,624 B1 | 10/2001 | Cuschieri et al. | |
| 6,443,944 B1 * | 9/2002 | Doshi et al. | 606/1 |
| 6,533,720 B1 * | 3/2003 | Dhindsa | 600/159 |
| 6,533,797 B1 * | 3/2003 | Stone et al. | 606/184 |
| 6,575,919 B1 | 6/2003 | Scribner et al. | |
| 6,620,184 B2 * | 9/2003 | de Laforcade et al. | 606/205 |
| 6,786,865 B2 * | 9/2004 | Dhindsa | 600/159 |
| 6,830,545 B2 * | 12/2004 | Bendall | 600/114 |
| 7,094,202 B2 | 8/2006 | Nobis et al. | |
| 2001/0018553 A1 | 8/2001 | Haan et al. | |
| 2002/0062065 A1 | 5/2002 | Daniel et al. | |
| 2002/0095177 A1 | 7/2002 | Kupferschmid et al. | |
| 2004/0220449 A1 * | 11/2004 | Zirps et al. | 600/104 |
| 2005/0070754 A1 | 3/2005 | Nobis et al. | |
| 2005/0070885 A1 | 3/2005 | Hess et al. | |

FOREIGN PATENT DOCUMENTS

| | | |
|---|---|---|
| EP | 0 908 141 A1 | 4/1999 |
| JP | 5-200038 | 8/1993 |
| JP | 2003-144444 | 6/2003 |
| WO | 02/06328 A2 | 1/2002 |
| WO | WO 02/39910 A2 | 5/2002 |

OTHER PUBLICATIONS

EPO Search Report dated Jan. 17, 2005 for corresponding patent application, European Patent Application No. EP 04 25 6010.
European Patent Office Communication dated Dec. 17, 2009 corresponding to the European Patent Application No. 04256001.1.

* cited by examiner

HANDLE FOR ENDOSCOPIC DEVICE

FIELD OF THE INVENTION

The present invention relates, in general, to medical devices, and more particularly to handles on endoscopic and surgical accessories.

BACKGROUND OF THE INVENTION

Endoscopists typically perform diagnosis and therapy using a flexible endoscope such as a gastroscope, colonoscope, enteroscope, cystoscope, or other types of endoscopes. The endoscope provides the endoscopist with the ability to visualize the inside of a lumen, and is often designed with an integral working channel through which small accessory devices may be passed to perform therapy at various tissue sites within a body.

Guiding the flexible endoscope to the desired location within a body lumen requires a high level of skill. For example, navigating a tortuous bending colon or introducing a gastroscope into an esophagus can be a difficult and time-consuming part of a procedure. Therefore, much of the endoscopist's skills are related to using and handling the endoscope. Unlike certain procedures in laparoscopic surgery where an assistant may hold the camera, use of a gastroscope typically requires that the endoscopist always maintain the scope with at least one hand, leaving only one hand to introduce and operate accessories through the integral working channel of the scope.

Current handle designs typically require the use of an operator's thumb to actuate the end effector. Among the current designs are pistol grips, syringe grips, and scissor grips. These existing designs do not allow an endoscopist to both feed and operate (e.g. slide, open, close, actuate, etc.) the accessory being used with the endoscopist's single free hand.

Therefore, an assistant is typically used to operate (slide, open, close, actuate) an accessory such as a forcep or snare to take biopsies or remove polyps. For example in a gastrointestinal procedure, a right handed endoscopist typically holds the endoscope controls in his/her left hand and may advance an accessory device into the working channel of the endoscope with the right hand by grasping the shaft of the accessory. An assistant, who stands close to the endoscopist, is employed to open, close, or otherwise actuate the accessory when given the verbal direction by the endoscopist. The endoscopist feeds the accessory to the desired tissue area using a combination of articulating the endoscope with the left hand and feeding the accessory forward with the right hand, and verbally signals the assistant when to open or close the jaws to remove a portion of tissue.

Although this procedure using an assistant is used, there may be delays or miscommunication between endoscopist and assistant as to when or where to operate an accessory that results in procedure delays, misdiagnosis, or incomplete tissue removal. Another issue that occasionally arises when using an endoscopic accessory is that winding or otherwise positioning a long, flexible accessory instrument in a tortuous path can result in a reduction in ability to open or close the end effector at the distal end of the device. This loss in the ability to open or close the device results from the free floating pull cable (typically inside a long flexible device) being placed in tension as the shaft is wound, causing the end effector to partially close independently of actuation of the handle. Such limitations in the end effector motion may reduce the ability to perform a procedure, or reduce the force with which jaws close, affecting an operator's ability to sample tissue adequately.

SUMMARY OF THE INVENTION

Applicants have recognized the desirability of having a handle and actuator that permits the endoscopist to both feed and operate the device with a single hand, which in turn can help minimize the potential for miscommunications with an assistant.

Applicants have also recognized the need for an actuating mechanism that permits a relatively long, flexible accessory instrument to be placed in a tortuous path, without losing the full range of actuation of the end effector due to movement of an internal pull member such as a pull cable or wire relative to an outer sheath of a flexible member, and which provides adequate stroke length to completely close the end effector of the accessory instrument, even when it is placed in a tortuous path.

In one embodiment, the present invention provides a handle for use with an endoscopic device. The handle is adapted for use with a single hand, the handle comprising: a housing adapted for gripping in the palm of a user's hand; and an actuator for actuating an end effector associated with the endoscopic device. The actuator is operable by one or more fingers of the same hand, wherein the actuator is operable without the use of either of the thumb and index finger of the same hand, and wherein the thumb and index finger of that hand are free to advance a portion of the endoscopic device through an endoscope.

In another embodiment of the present invention, a method of operating an endoscopic device is provided, including the steps of: holding a handle of the device between the palm and at least one finger of the hand other than the index finger and thumb; holding a portion of a flexible shaft extending from the handle between the thumb and another finger of the same hand holding the handle; advancing the flexible shaft using at least the thumb of the same hand holding the handle; and operating an actuator associated with the handle with the same hand holding the handle without using the thumb of that hand to operate the actuator.

The present invention also provides a method comprising the steps of: providing an endoscope having at least one channel; providing an endoscopic accessory comprising a flexible member (such as a flexible shaft), a handle associated with a proximal end of the flexible member, and an end effector associated with a distal end of the flexible member; steering the distal end of the endoscope with one hand; holding the handle of the endoscopic accessory in the other hand; advancing the endoscopic accessory through a channel of the endoscope with the hand holding the handle and while holding the handle; and actuating the end effector of the endoscopic accessory with the hand holding the handle while holding the handle.

The present invention also provides a medical device comprising: a flexible member, such as a flexible shaft with a pulling member (such as a wire or cable) movable therein; an actuating mechanism operatively associated with a proximal end of the flexible shaft; and an end effector associated with the distal end of the flexible shaft. The end effector can be operatively associated with a distal end of the pulling member; and the actuator mechanism can have a first configuration in which the actuator mechanism is decoupled from the pulling member, and a second configuration wherein the actuator mechanism becomes operatively coupled to the pulling member to operate the end effector. Decoupling the actuator mechanism from the pulling member in the first configuration enhances the ability of the flexible shaft to take on a tortuous path while maintaining good end effector actuation.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

Figure 1:
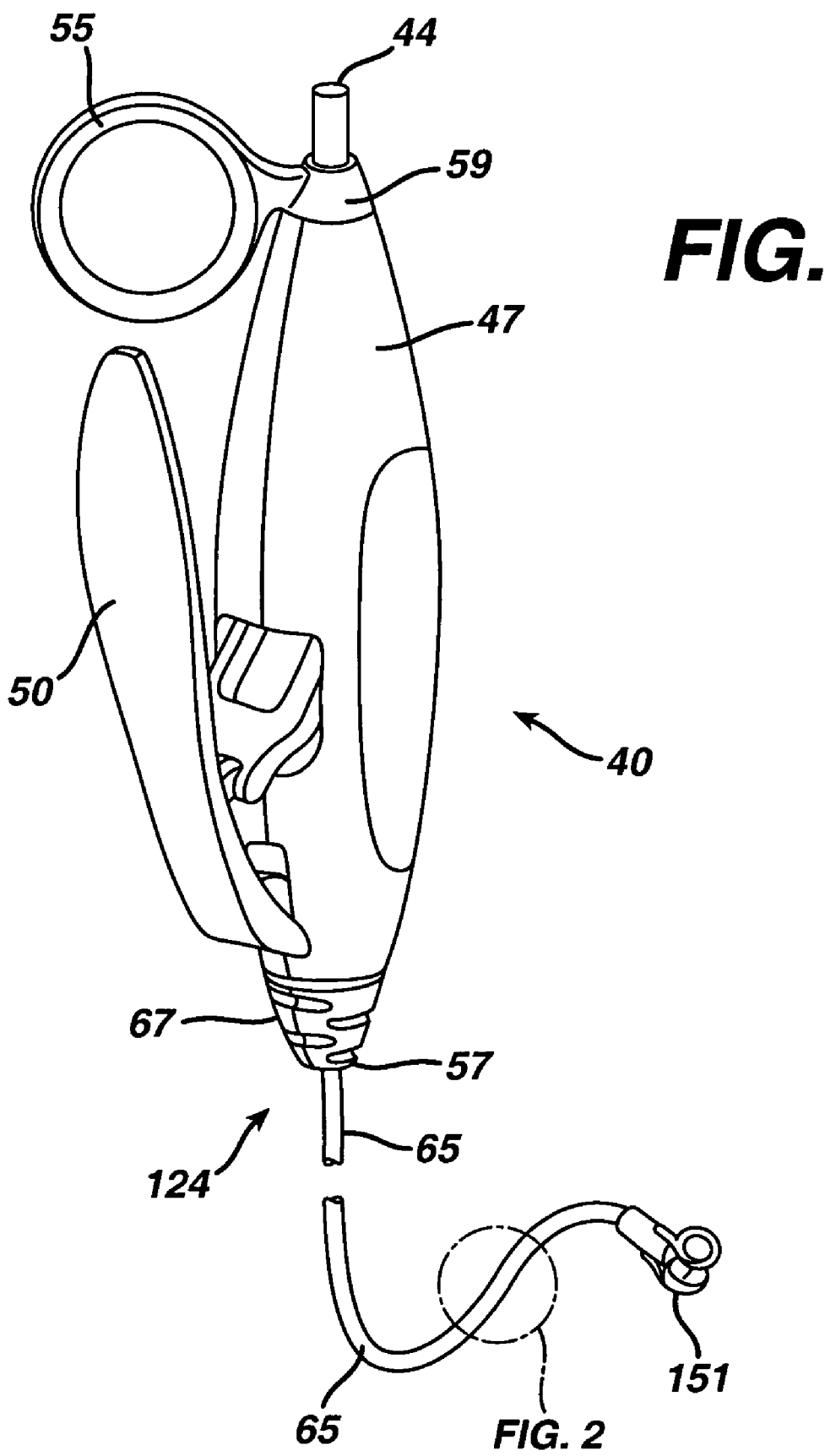
FIG. 1 is an illustration of a medical device handle 40 associated with a proximal end of a flexible endoscopic accessory 124 having a pair of biopsy jaws 151.

FIG. 1 shows a novel medical device handle 40 according to the present invention associated with the proximal end of an endoscopic accessory instrument 124. The accessory 124 illustrated in FIG. 1 includes a biopsy jaw pair 151 (also referred to as biopsy jaws 151) at the distal end of the accessory 124. For illustrative purposes, the description that follows uses biopsy jaws 151 as an example of a suitable end effector on endoscopic accessory 124, but it is apparent to those skilled in the art that handle 40 may be used with other accessory instruments having other end effectors or other devices positioned at the distal end of accessory 124 for providing diagnostic and/or therapeutic function(s), such as, but not limited to, biopsy forceps such as biopsy jaws 151, grasping forceps, surgical scissors, extractors, washing pipes and nozzles, needle injectors, non energized snares, and electrosurgical snares.

Figure 15A:
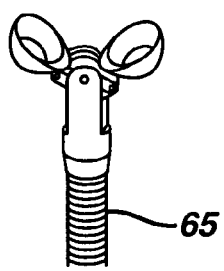
FIG. 15A-I illustrates various endoscopic end effectors.
Figure 15B:
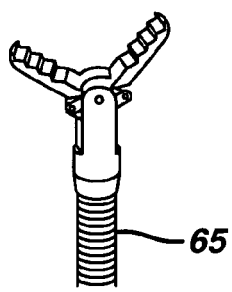
Figure 15C:
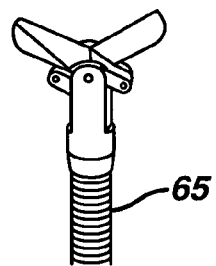
Figure 15D:
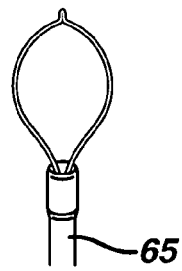
Figure 15E:
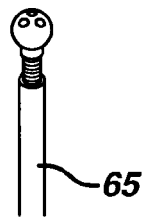
Figure 15F:
Figure 15G:
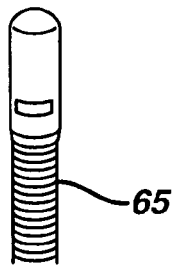
Figure 15H:
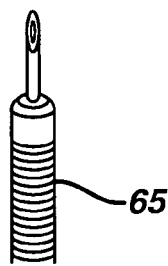
Figure 15I:
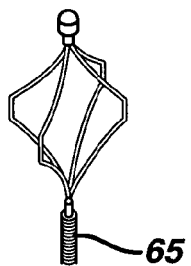

FIGS. 15A-15I illustrate various end effectors. FIG. 15A illustrates a biopsy forceps for taking and removing from the body a tissue sample, similar to the biopsy jaws 151 illustrated in FIG. 1. FIG. 15B illustrates a tissue grasper, which can be used to grasp tissue for pulling or moving the tissue. FIG. 15C illustrates surgical scissors for cutting tissue. FIG. 15D illustrates a surgical snare, which can be an electrosurgical snare or a non-energized snare. FIG. 15E illustrates a tissue coagulation electrode of the type having suction holes at the tip. FIG. 15F illustrates a spraying nozzle, which can be used for washing a tissue site or delivering a diagnostic or therapeutic substance to a tissue site. FIG. 15G illustrates a magnetic extractor for extracting magnetic objects from a tissue site. FIG. 15H illustrates a needle injector for providing injection capability at a tissue site. FIG. 15I illustrates a retrieval basket for capturing and retrieving a tissue sample from inside the body. The end effector employed at the distal end of accessory 124 can be used for various diagnostic and/or therapeutic procedures, including without limitation cutting tissue, grasping tissue, piercing tissue, injecting tissue with a substance, extracting objects from tissue sites, visualizing or magnifying a tissue image, and cauterizing or ablating tissue.

Generally, handle 40 can include a housing 47, an actuation mechanism including an actuator 50 shown in the form of an actuator lever, and an attachment 57 to a flexible member, such as flexible shaft 65. Other embodiments of handle 40 may include a swivel ring 55 and a release 44. Flexible shaft 65 can be at least 0.5 meters long, and more particularly at least about 1 meter long.

The housing 47 can have a generally smooth shape that is comfortable to hold within a human hand during an endoscopic procedure, such as but not limited to: a barrel shape, torpedo shape, or generally cylindrical shape, which shapes can have a longitudinal axis, with one or both ends being rounded or tapered so that the portion of the handle having the maximum diameter (or other maximum width dimension) is positioned intermediate the proximal and distal ends of the handle. The housing 47 can be shaped to fit in the palm of the users hand such that the thumb and index finger are positioned away from the attachment 57 to the flexible shaft 65.

Housing 47 can have a hollow shell construction formed of two half shells. Housing 47 supports the actuation mechanism (shown in more detail in FIGS. 8 through 12) that causes biopsy jaws 151 to open or close when actuator lever 50 is moved. Housing 47 may be molded, cast, or machined from any suitable material, including without limitation plastics or metals. For example, housing 47 can be formed from polycarbonate (such as is available as Calibre 2061 from Dow Plastics, Midland, Mich.) or aluminum. Housing 47 may also comprise a relatively soft, comfortable gripping surface made from a material such as Santoprene 281-55 Rubber available from Advanced Elastomer Systems, Akron Ohio on the exterior surface of housing 47 to facilitate holding by the endoscopist.

Actuator 50 can be pivotably supported adjacent the end of housing 47 associated with flexible shaft 65, which end can be the distal end of the housing 47. Acuator 50 can be pivotably supported at an actuator pin 62 (see FIG. 8). Actuator 50 may be made from any suitable material, including a plastic such as polycarbonate, or metal such as aluminum. In one embodiment, the position of actuator 50 can be biased (such as with a spring) to be in an open position so that squeezing of actuator 50 toward housing 47 causes the actuation mechanism to close biopsy jaws 151.

The distal end of housing 47 includes attachment 57 to flexible shaft 65. Attachment 57 may include a strain relief component that prevents flexible shaft 65 from breaking at the point where shaft enters or is otherwise connected to housing 47. For example, a rubber or rubber like boot 67 may be used for this purpose at attachment 57. Boot 67 may be molded from a soft flexible material such as Silastic silicone Q7-4535 (Dow Corning Midland, Mich.).

Figure 7:
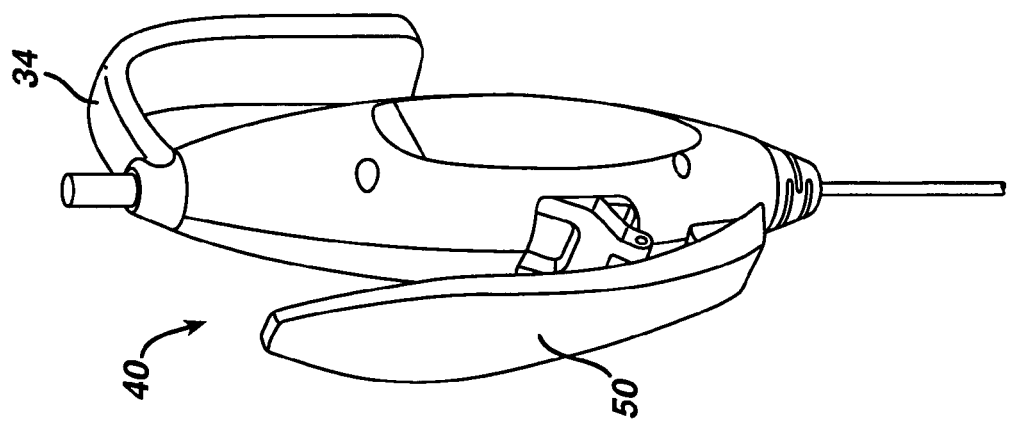
FIGS. 5, 6, and 7 illustrate alternative embodiments of handle 40 with various means for attaching handle 40 to a hand without gripping with fingers.
Figure 6:
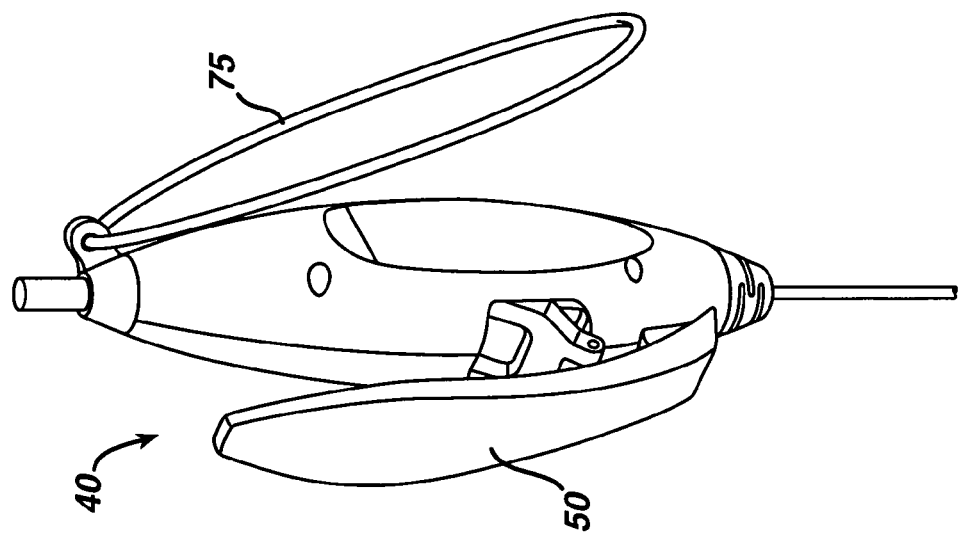
Figure 5:
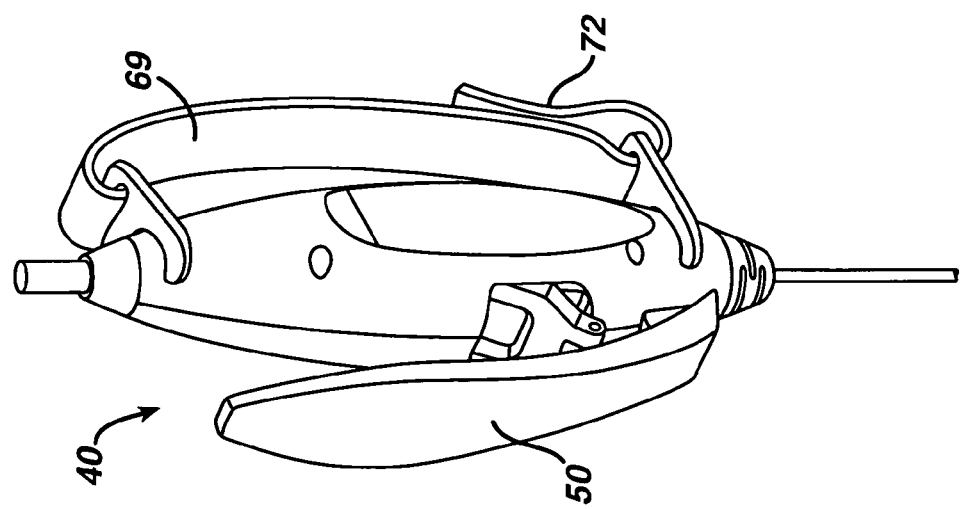

Still referring to FIG. 1, swivel ring 55 is one embodiment of a means for holding handle 40 without gripping with fingers. Swivel ring 55 may be attached to a proximal end of housing 47, and may also be molded, cast, or machined from a plastic or metal such as those described for use in housing 47. A swivel joint 59 may allow a full 360 degree rotation of swivel ring 55 with respect to housing 47 for ease of manipulation within the hand. Other embodiments of a means for holding handle 40 to a hand without gripping with fingers are shown in FIGS. 5, 6 and 7.

Figure 14:
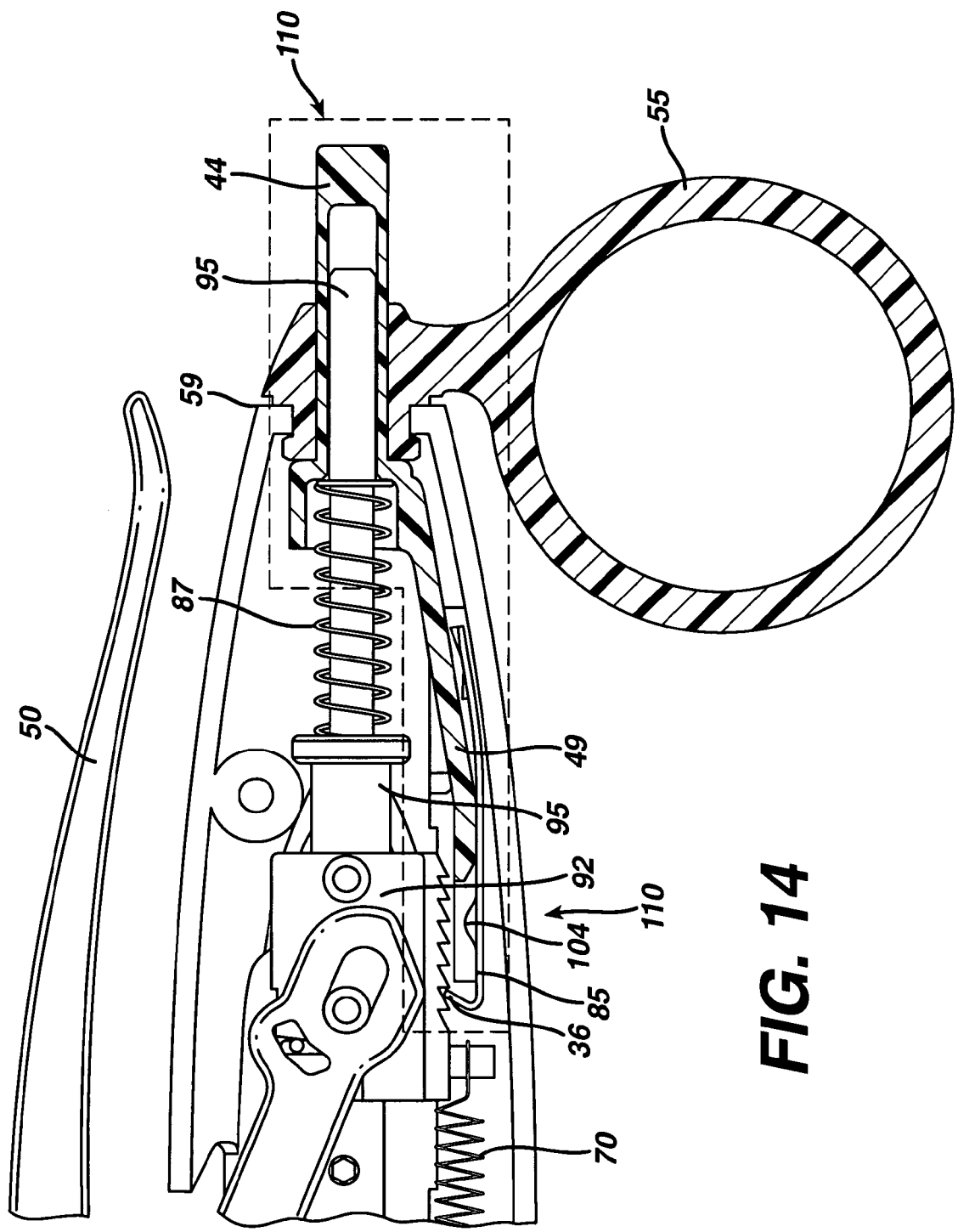
FIG. 14 is a detail cross section view of a ratchet mechanism 110 showing the proximal portion of handle 40 including a return spring 87 seated within a release 44.

A release 44 can be provided for opening biopsy jaws 151 if a ratchet mechanism or other equivalent means is employed to maintain biopsy jaws in a closed configuration when actuator lever 50 is partially or completely depressed. A ratchet mechanism 110 is illustrated in FIG. 14. Release 44 can extend from the proximal end of housing 47. In the embodiment shown in FIG. 14, when actuator lever is 50 is depressed, ratchet mechanism 110 is engaged to hold biopsy jaws 151 closed or partially closed. Release 44, which may be in the form of a button, slider, switch, or other suitable release member, is used to disengage ratchet mechanism 110 to allow actuator 50 and biopsy jaws 151 to open.

Figure 2:
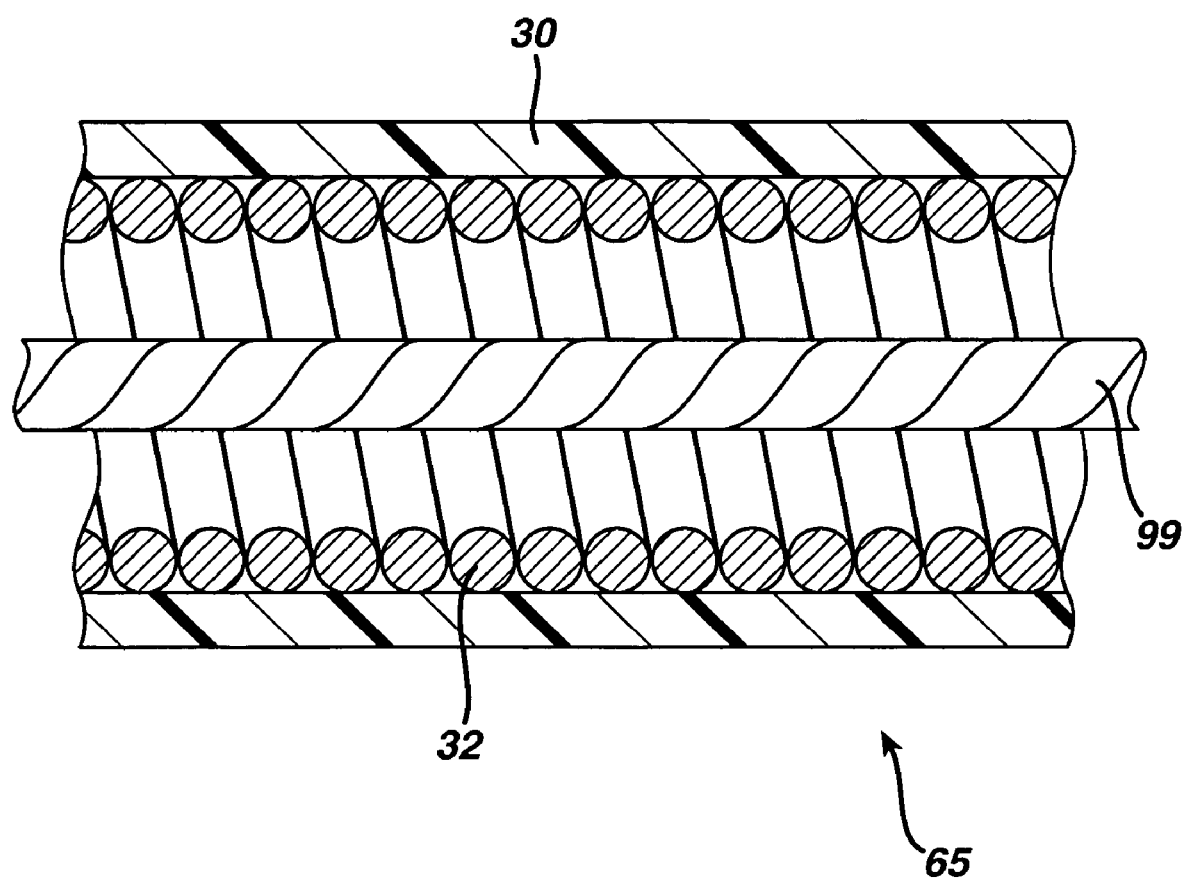
FIG. 2 shows a cross section of a known flexible shaft construction.

FIG. 2 illustrates a suitable construction of flexible shaft 65 which is known in the art for use with flexible endoscopic instruments. The flexible shaft comprises an outer sleeve 30, a tightly wound spring 32, and a pulling member such as a pull cable 99. Pull cable 99 floats freely within the inner diameter of spring 32. Tension applied to cable 99 can be used to actuate certain end effectors which may be disposed at the distal end of shaft 65 (e.g. to close biopsy jaws, forceps jaws, etc.). In embodiments of the present invention, the proximal end of pull cable 99 can be operatively associated with the actuation mechanism within the housing 47, and a distal end of pull cable 99 can be operatively associated with an end effector such as biopsy jaws 151.

Figure 3:
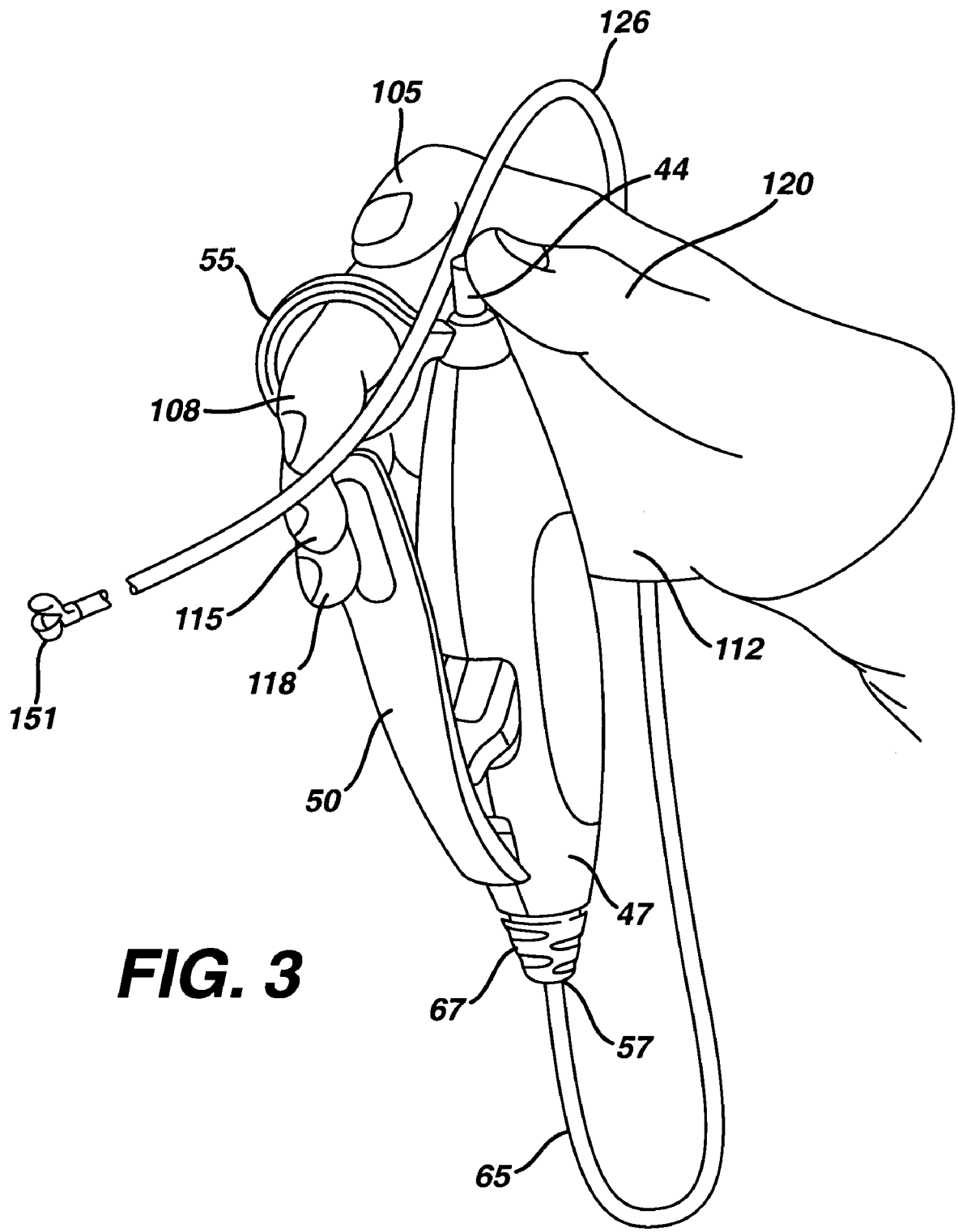
FIG. 3 illustrates an arrangement of handle 40 in an endoscopist's hand that allows actuation of biopsy jaws 151 between the palm 112 and fourth finger 115 of a user and forward advancement of the flexible shaft with the user's thumb 120 and index finger 105 of the same hand.

FIG. 3 shows housing 47 comfortably residing in an endoscopist's hand. Housing 47 and actuator lever 50 are positioned between the palm 112 and the forth finger 115 and fifth finger 118 of that hand to actuate closure of the end effector, with the thumb 120 and index finger 105 positioned above (proximally of) the actuator lever 50 in FIG. 3. A third middle finger 108 of the same hand may be inserted through swivel ring 55 to enable the user to hold the endoscopic device 124 without grasping the handle 47 with multiple fingers, so that other fingers are free for other actions. The thumb 120 and index finger 105 of the same hand are free to pinch shaft 65 of the endoscopic accessory 124 for advancing it through a working channel 133 of an endoscope 128 (shown in FIG. 4). Handle 40 is adapted to be held such that the smaller fingers (i.e. the fourth and fifth fingers 115 and 118) are positioned relatively closer toward the distal end of the handle 40 associated with flexible cable 65, while the larger fingers (i.e. the thumb and index finger) are positioned relatively closer toward the proximal end of the handle 40. When handle 40 is grasped between the palm and smaller fingers of the hand, the thumb of that hand points in a generally proximal direction, and generally opposite to the direction in which flexible shaft 65 extends from handle 40. Also, the thumb and index finger are positioned proximal of the free end of actuator lever 50.

As shown in FIG. 3, shaft 65 may be formed in a loop 126 behind the hand and may then be pinched in between the thumb 120 and index finger 105 to feed forward into working channel 133. Release 44, which can be in the form of a plunger like button, resides in an area that is accessible by thumb 120 for disengagement of ratchet mechanism 110 (FIG. 14), such as at the proximal end of handle 40.

Figure 4:
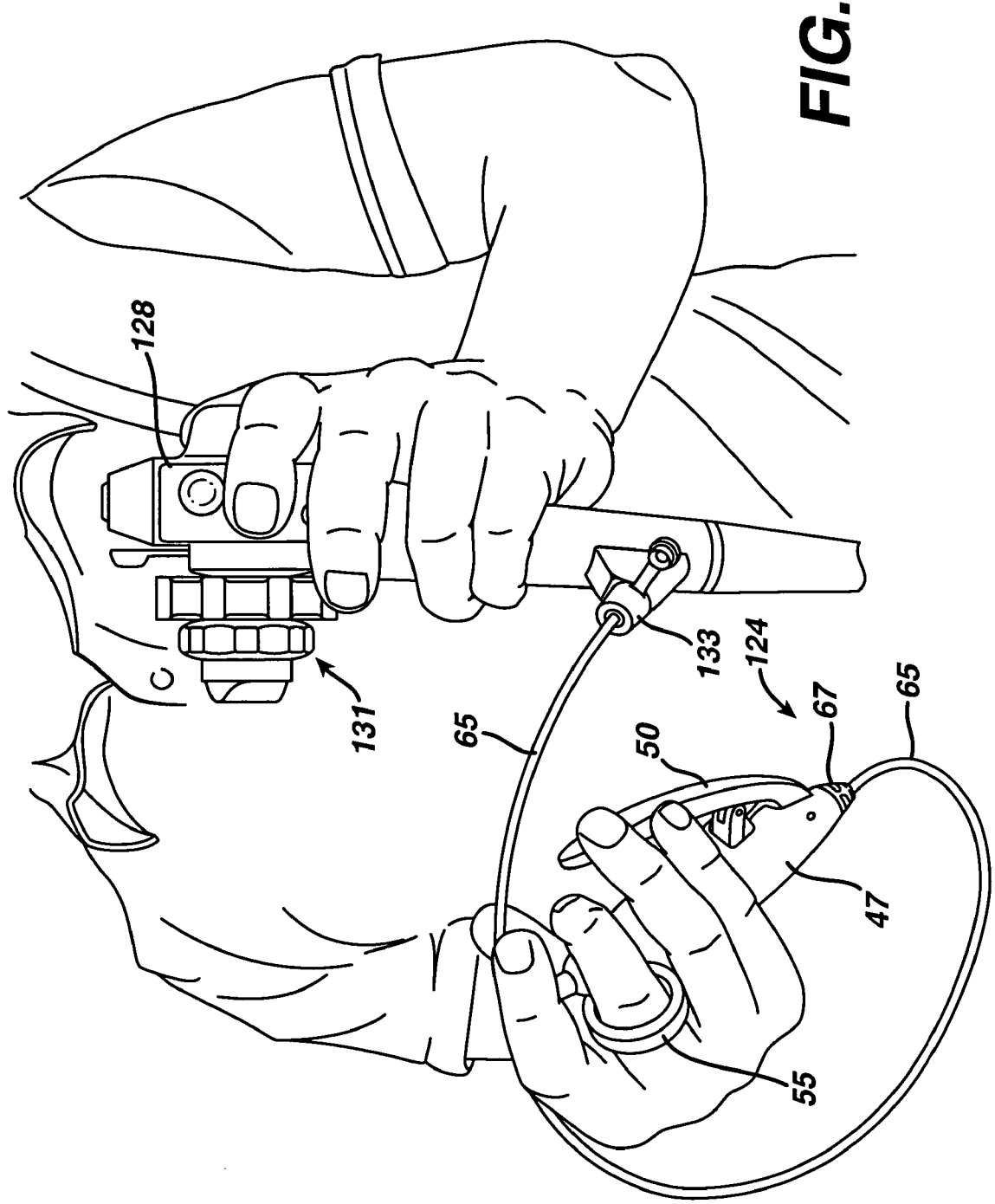
FIG. 4 is an illustration of an endoscopist's hand positions while using an endoscope 128 and endoscopic accessory 124 with handle 40.

FIG. 4 depicts hand positions that may be used by a right handed endoscopist while using endoscope 128 and endoscopic accessory 124 with handle 40. The left hand is typically used to operate an articulation control 131 on endoscope 128. Endoscopists may practice extensively to hone their skills in manipulating these controls to navigate the body lumen, such as a colon. Because the procedure success is highly dependent upon the view seen by the camera located at the distal end of endoscope 128, the endoscopist typically does not give up control of an articulation control 131 during the procedure. Therefore, only one hand is typically available to operate endoscopic accessory 124.

Endoscopic accessories with existing handle designs, such as pistol grips, scissor grips, or syringe grips, use the thumb 120 to operate (open/close/slide) the end effector. Therefore, the endoscopist uses his or her free hand to feed shaft 65 of endoscopic accessory 124 through working channel 133 of the endoscope 128 while giving verbal cues to an assistant to open or close biopsy jaws 151. Prior handle configurations are not used by the endoscopist to operate the end effector with the same hand used to advance the end effector into working channel 133. Handle 40 of the present invention is useful in giving control of the advancement and actuation of the endoscopic accessory 124 to the endoscopist, to thereby reduce or eliminate any delay or miscommunication with an assistant.

FIGS. 5, 6 and 7 illustrate alternative embodiments of handle 40 with alternative means for attaching to a hand without gripping with fingers. FIG. 5 shows handle 40 with a strap 69 made from a durable textile, such as nylon. Strap 69 may be tethered to housing 47 at two or more points, and may be made adjustable in size by the use of an attachment section 72 of hook-and-loop material such as Velcro brand fastener. FIG. 6 depicts a looped strap 75 that could be used to hold handle 40 to the hand. FIG. 7 shows another alternative of handle 40 using a malleable hook 34 that can be formed into a shape to conform to the hand so that it can remain attached without gripping with fingers.

Figure 8:
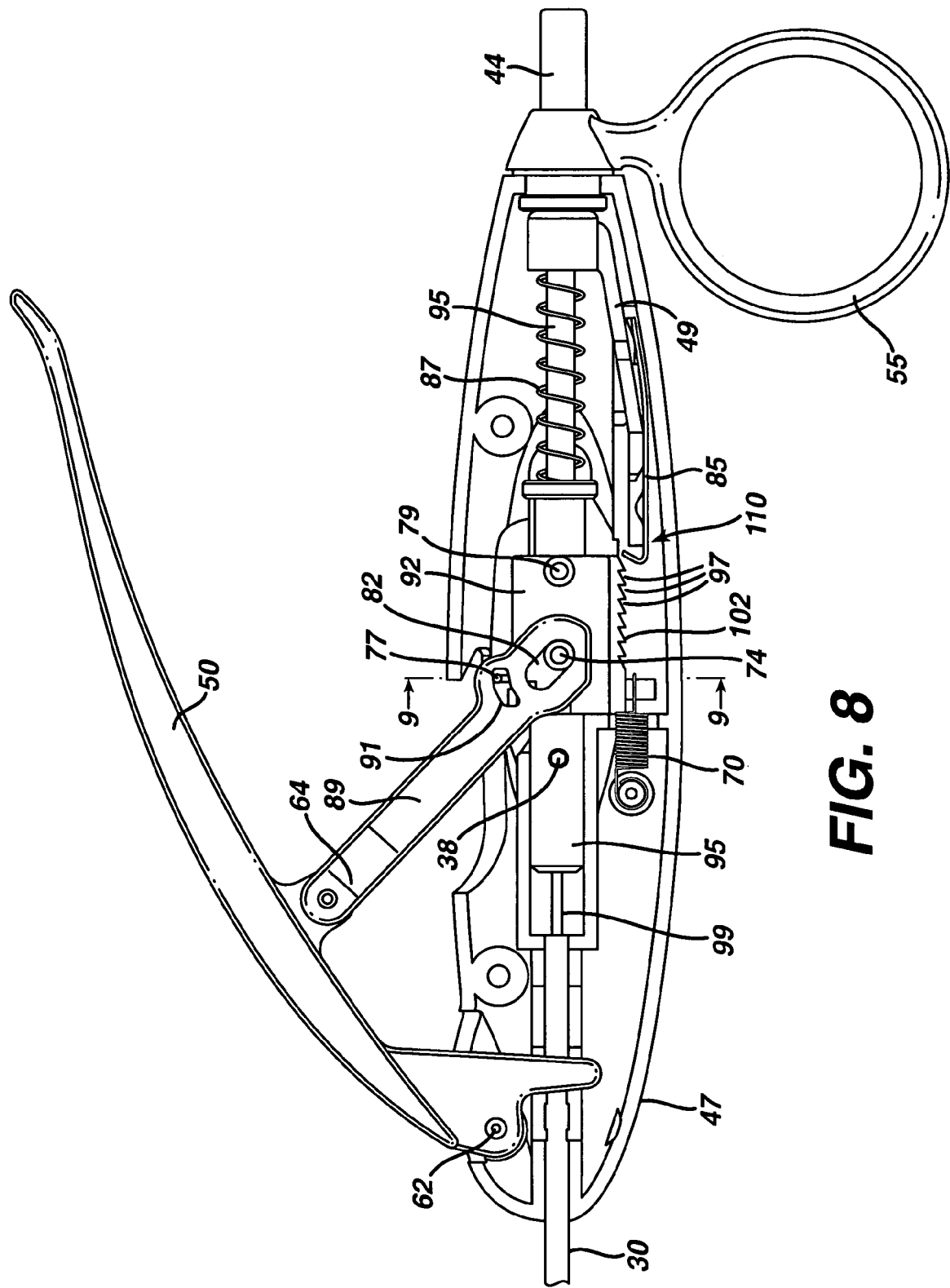
FIG. 8 is a sectional view of one embodiment of an actuation mechanism 80 within handle 40 of FIG. 1 in a completely open position.

FIG. 8 shows a side view of a cut away of one embodiment of an actuating mechanism which may be used to operate the end effector disposed at the distal end of the flexible shaft 65. In FIG. 8, the actuator lever 50 is in a first position, fully open, and the actuating mechanism is shown in a first configuration, corresponding to the biopsy jaws 151 being open, and with no tension applied to cable 99 by the actuation mechanism and no engagement of the actuation mechanism with the pulling member.

The embodiment of the actuation mechanism in FIGS. 8-12 includes a drive link 89 (also referred to as link 89), a torsion spring 77, a spring block 92, and a return spring 87. A wire sleeve 95, which is fixedly attached to the proximal end of pull cable 99, can be engaged by torsion spring 77 when spring 77 is compressed.

Also shown are components of a ratchet mechanism 110 that may be used to hold biopsy jaws 151 closed or partially closed upon compression and release of actuator lever 50. Ratchet mechanism 110 includes a leaf spring 85 having a pawl 36 associated with the free end of the spring 85, and a release 44 to disengage pawl 36 from a rack 102 supported on a spring block 92.

Figure 12:
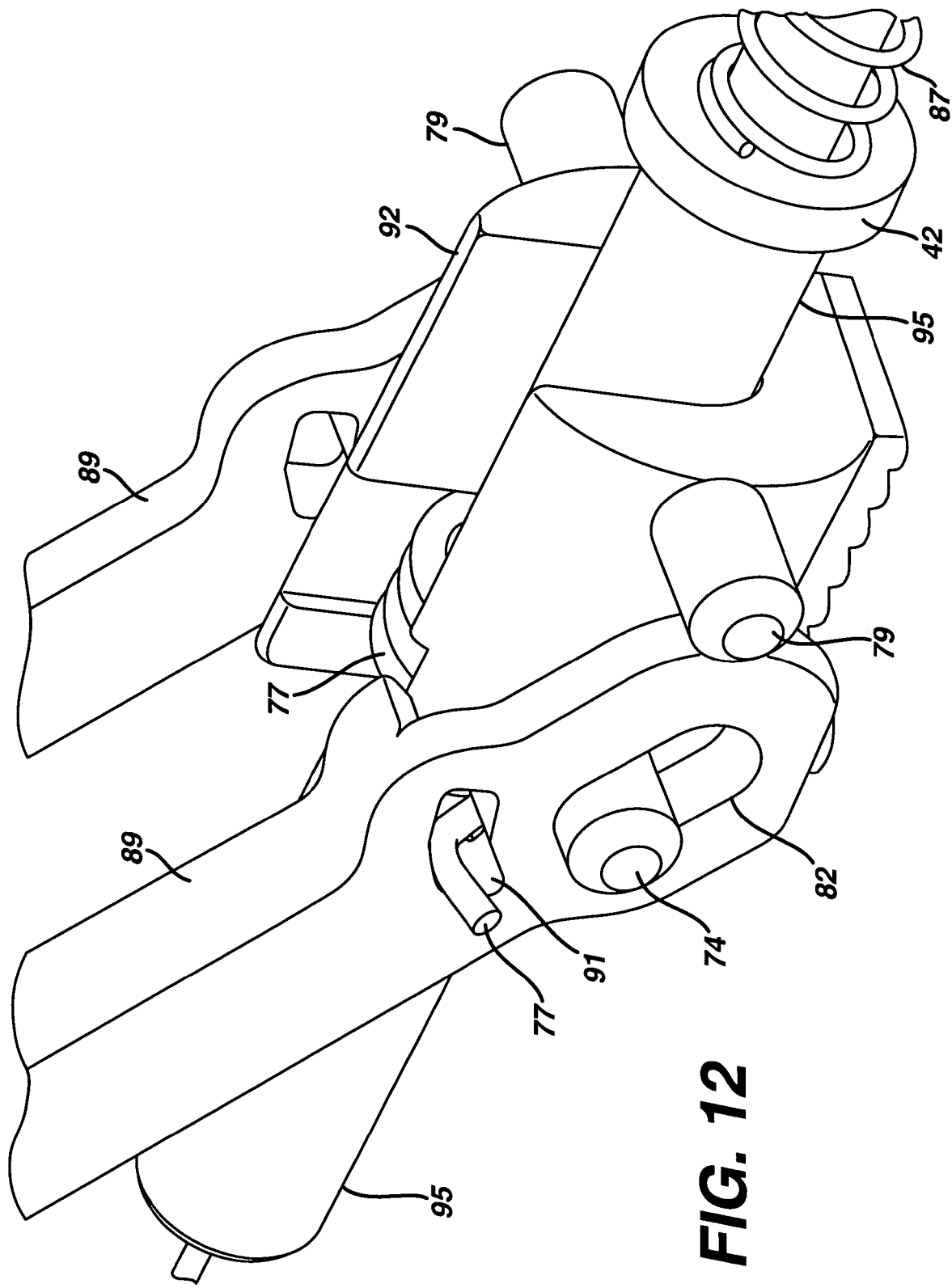
FIG. 12 shows an isometric view of torsion spring 77 and wire sleeve 95 when actuator 50 is in the position shown in FIG. 10.

Link 89 is shown pivotably connected at a first end to actuator 50 by a link pin 64. The opposite second end of link 89 is shown operatively associated with spring block 92 by a distal block pin 74 extending through link gripping slot 82, which slot 82 extends through link 89 near the second end of link 89. As shown in FIG. 12, the second end of link 89 can have a forked or clevis like configuration, and a slot 82 can be disposed in each fork or clevis arm, with each slot 82 engaging a pin 74. Link 89 may be machined or cast from metal such as stainless steel or aluminum.

Link 89 transfers the force from actuator 50 to first cause closure of torsion spring 77 about wire sleeve 95 (which sleeve 95 is fixed to the proximal end of pull cable 99), and then to provide sliding of spring block 92 toward the proximal end of handle 40, ultimately to provide closure of the end effector operatively associated with the distal end of flexible shaft 65. A stroke length applied to pull cable 99 of approximately 0.200 inches to 0.600 inches is appropriate for use in closing biopsy forceps 151. In one embodiment, the actuating mechanism can provide a range from about 0.400 to 0.450 inches for closing biopsy forceps 151.

Figure 9:
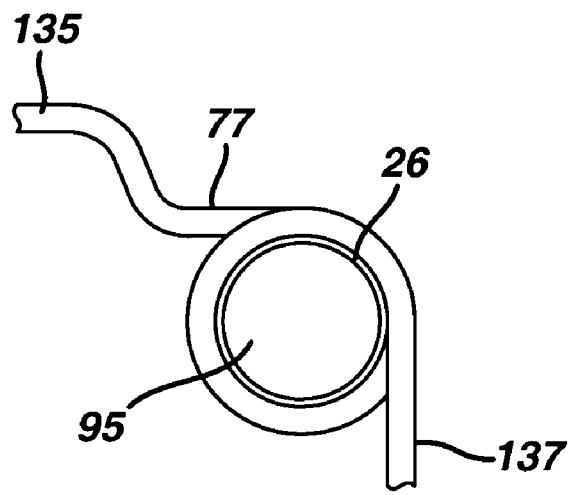
FIG. 9 is a cross section view taken at line 9-9 of FIG. 8 showing the orientation of a torsion spring 77 and a wire sleeve 95 when an actuator 50 is in a completely open position.
Figure 11:
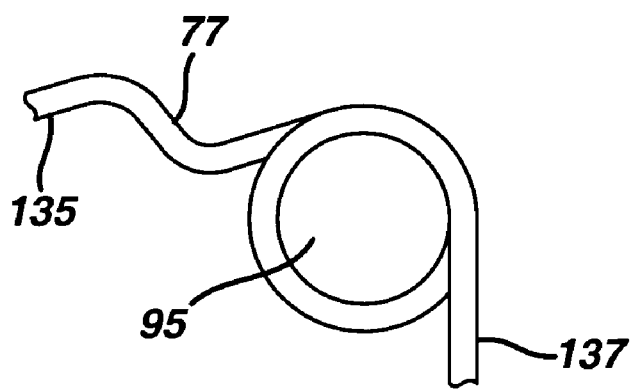
FIG. 11 is a cross section view taken at line 11-11 of FIG. 10 showing torsion spring 77 engaging wire sleeve 95.

Referring to FIG. 9, when actuator lever 50 is in the first open position, (as shown in FIG. 8), there is a clearance 26 between wire sleeve 95 and the inner diameter of torsion spring 77. The magnitude of this clearance may be about 0.025 to about 0.050 inch in one embodiment. This clearance 26 allows wire sleeve 95 to float freely inside torsion spring 77 as flexible shaft 65 is wound into a tortuous path. Because wire sleeve 95 is decoupled from torsion spring 77 until actuator lever 50 is depressed a predetermined distance corresponding to closure of the spring 77 on sleeve 95, the actuation mechanism does not hold or otherwise constrain sleeve 95 and pull cable 99 when the actuator lever 50 is in the open position. As a result, flexible shaft 65 can be wound or otherwise placed in a tortuous path without causing closing of the biopsy jaws 151. Cable 99 and sleeve 95 are not mechanically coupled to the actuation mechanism with lever 50 in the full open position. With lever 50 in the full open position, and cable 99 and sleeve 95 can move proximally or distally relative to handle 40 and outer sleeve 30. It is not until lever 50 is closed sufficiently such that spring 77 grips sleeve 95 that the proximal end of cable 99 and sleeve 95 are constrained by the actuation mechanism. Therefore, a full throw of lever 50 provides a full range of motion of the end effector even when shaft 65 is placed within a tortuous path.

Torsion spring 77 can have a wire diameter of about 0.025 inch to about 0.060 inch, and in one embodiment is made from spring wire having a diameter of 0.0385 inch. Torsion spring 77 may be coiled about 3 times and the inner diameter of the coil may range from 0.100 inch to 0.500 inch in the non compressed state, with the uncompressed inner diameter being about 0.250 inch in one embodiment. The spring arms extending from each end of the coil may have a length from 0.100 inch to 0.400 inch so that they may be fixed or moved to cause the spring inner diameter to change. When the arms are squeezed, the inner diameter of the spring coil is reduced, such as from 0.250 inch to about 0.200 inch, or by an inner diameter reduction of about 0.050 inch. In such an embodiment, a sleeve 95 residing within the coil and having a diameter slightly greater than about 0.200 inch can be gripped by the compressed spring in this embodiment. One suitable spring 77 is available from the McMaster-Carr (Aurora, Ohio) catalog as part number 9287K81.

Figure 10:
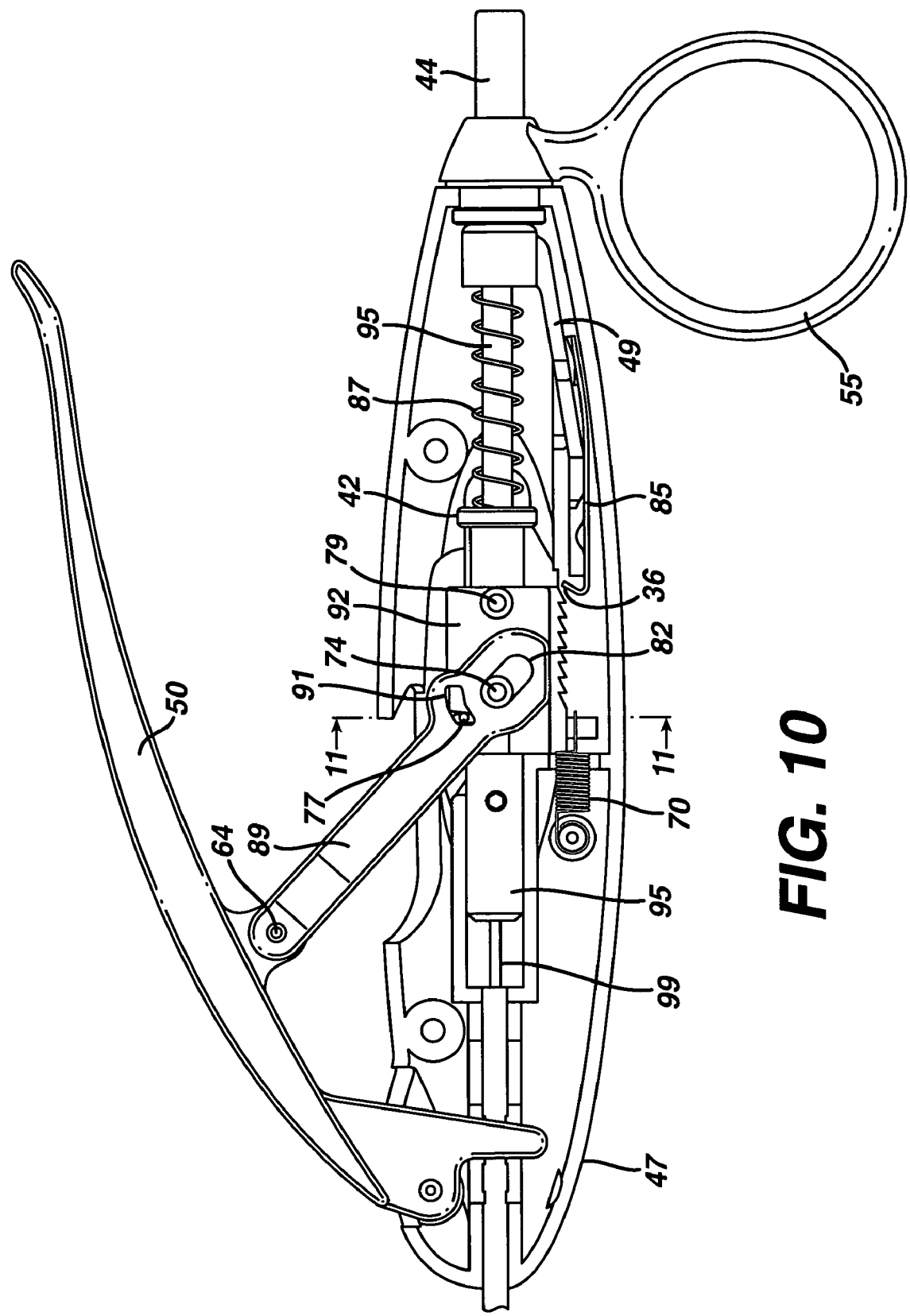
FIG. 10 is a sectional view of actuation mechanism 80 within handle 40 in a position that begins engagement of torsion spring 77 to wire sleeve 95.

FIG. 10 shows a side cut away view of the actuator lever 50 in a second partially closed position, and the actuation mechanism in a second configuration, with torsion spring 77 just gripping wire sleeve 95 (see FIG. 11), so that the actuation mechanism engages the pulling member. A spring compression slot 91 in link 89 is present to capture a closure arm 135 of torsion spring 77, so that as actuator 50 is depressed, link 89 slides down on distal block pin 74, and compresses torsion spring 77 (see FIG. 11). A fixed arm 137 of torsion spring 77 can be fixed to, disposed in, or otherwise constrained by spring block 92.

FIG. 12 is an isometric detail view of wire sleeve 95, spring block 92, torsion spring 77, and clevis arms of link 89. Wire sleeve 95 can have a generally cylindrical body having an outer diameter that allows it to fit within torsion spring 77 when spring 77 is not compressed. The distal end of wire sleeve 95 can be joined to the proximal end of pull cable 99 by any suitable means, such as by a set screw 38 (shown in FIG. 8), or by crimping, welding, brazing, or other fastening means. Sleeve 95 provides a larger diameter gripping surface than would be provided by pull wire 99. A shoulder 42 disposed on wire sleeve 95 provides a surface against which return spring 87 can be compressed, so that actuator 50 is biased to an open position when not actively squeezed or held by ratchet mechanism 110. Wire sleeve 95 may be cast or machined from a metal such as stainless steel or aluminum. In the embodiment shown, the diameter of the distal portion of wire sleeve 95 which resides within torsion spring 77 may be about 0.220 inch, the shoulder 42 may have a diameter of about 0.3250 inch, and the proximal portion that fits within return spring 87 may have a diameter of about 0.1250 inch.

Spring block 92 may be made from a dense plastic such as Ultem 2100 (General Electric Plastics, Pittsfield, Mass.), or from metal such as stainless steel. As actuator 50 is depressed, spring block 92 is constrained to move toward the proximal end of handle 40 along the longitudinal axis of the handle 40, with proximal block pins 79 and distal block pins 74 riding in parallel grooves or other suitable features which can be formed on the inside surface of housing 47. Spring block 92 may include a rack 102 comprising a plurality of teeth 97. As spring block 92 slides back toward the proximal end of housing 47, rack 102 is engaged by pawl 36 of leaf spring 85 to hold the end effector in a closed or partially closed position. Leaf spring 85 is formed from spring steel, and may have a thickness of about 0.02 inch.

Figure 13:
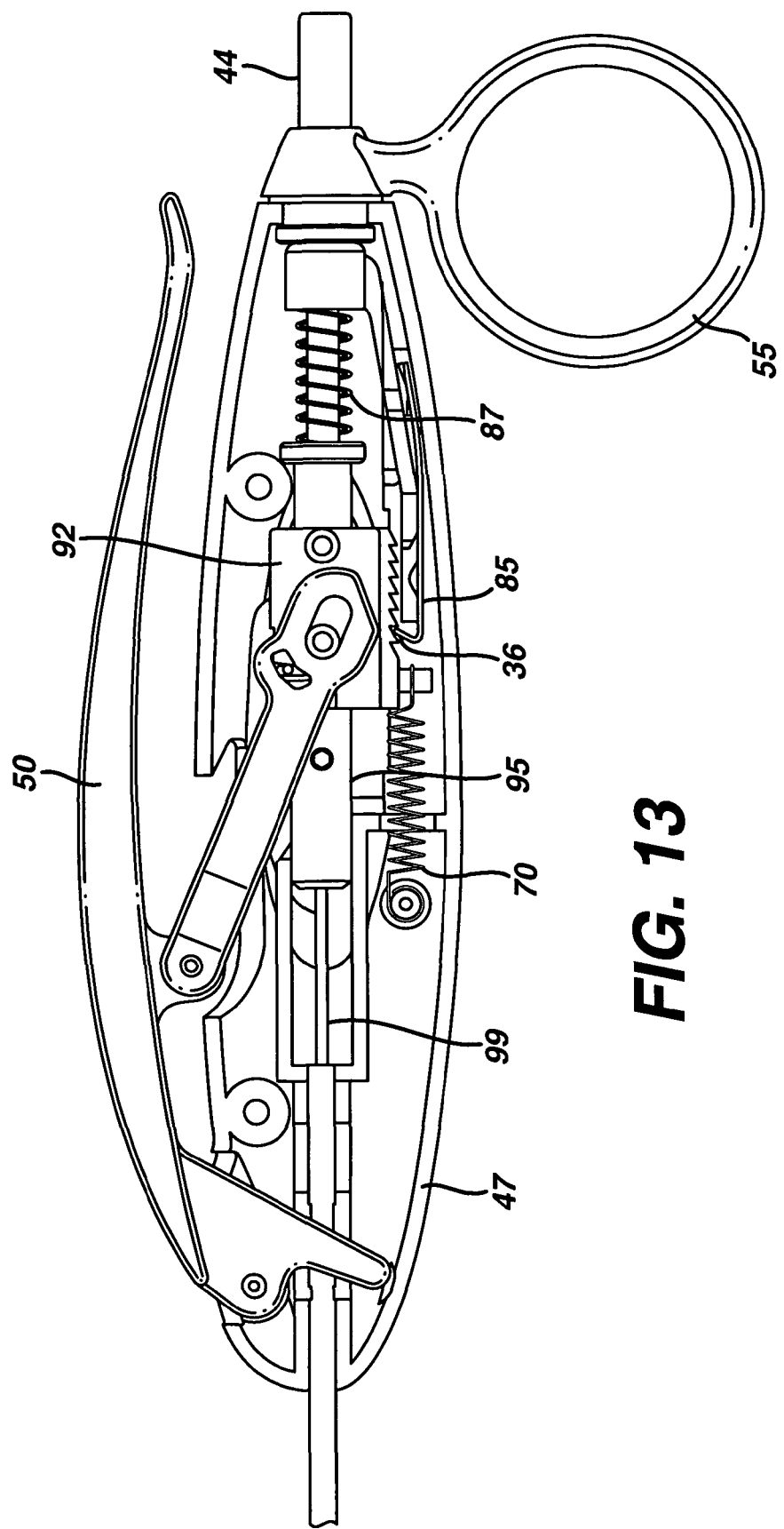
FIG. 13 is a sectional view of actuation mechanism 80 within handle 40 when actuator 50 is in the completely closed position.

FIG. 13 is a cut away view of handle 40 showing a third configuration of the actuation mechanism when actuator 50 is in a third, completely closed position. This view shows wire sleeve 95 translated along the axis of the handle 40 toward the proximal end of handle 40, with the actuator mechanism applying the maximum tension on pull cable 99 to close the end effector. In FIG. 13, return spring 87 is compressed, and a distal return spring 70 is stretched, both of which act to bias actuator lever 50 toward the open position. If a ratchet mechanism 110 is not employed, the actuator lever can be held in the closed position by the palm and small finger 118 to keep the end effector closed.

Return spring 87 may be made from 0.016 inch wire and have an outer diameter of about 0.200 inch. A suitable return spring 87 is available from McMaster-Carr (Aurora, Ohio) as part number 9657K66. Distal return spring 70 may also have a wire diameter of about 0.016 inch, and an outer diameter of about 0.125 inch. A suitable distal return spring 70 is available from Lee Spring Company (Brooklyn, N.Y.) as part number LE-016A-002.

Figure 16:
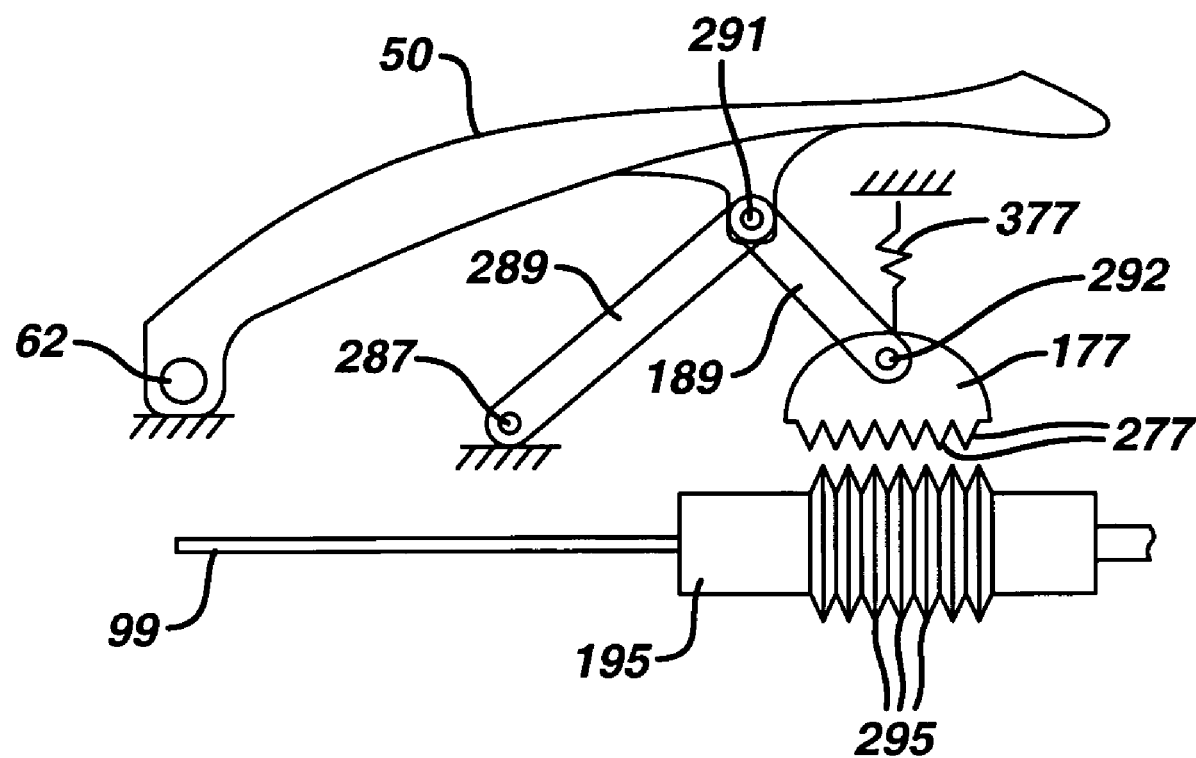
FIG. 16 illustrates a portion of an actuation mechanism in an alternative embodiment of the present invention employing interlocking features such as teeth to couple the actuation mechanism to the pulling member.

FIG. 16 illustrates an alternative embodiment for providing coupling and decoupling of the actuation mechanism with the pull member. In FIG. 16, actuator lever 50 is pivotably pinned with respect to housing (housing 47 represented schematically in FIG. 16) such as by pin 62, and pivotably pinned to link 189 and link 289 at pin 291. Link 289 is shown pivotably pinned to the housing by pin 287. Link 189 extends from actuator lever 50 to be pivotably pinned to sleeve engagement member 177 at pin 292. Sleeve engagement member 177 has teeth 277 (or other suitable surface features) for engaging complimentary teeth 295 on wire sleeve 195. Wire sleeve 195 is joined to the proximal end of pull wire 99, such as with a set screw or by bonding wire 99 to sleeve 195. Wire sleeve 195 is constrained by guide grooves, pins, or other suitable means such as can be provided on the inside of housing 47, so that sleeve 195 moves along an axis which can be generally parallel to the longitudinal axis of handle 40. Upon squeezing actuator 50 from an open position to a closed position, link 189 urges member 177 downward to engage sleeve 195, against a biasing force provided by spring 377. Spring 377 can be a coil spring or leaf spring which is connected to a portion of the housing. Spring 377 acts to separate member 177 from sleeve 195 when the actuator lever 50 is in the open position. Once member 177 engages sleeve 195, further closing of actuator lever 50 (by squeezing actuator lever 50 toward housing 47) causes link 189 to drive sleeve 195 in a proximal direction (to the right in FIG. 16) along the longitudinal axis of the handle 40, thereby providing tension to pull wire 99.

Figure 17:
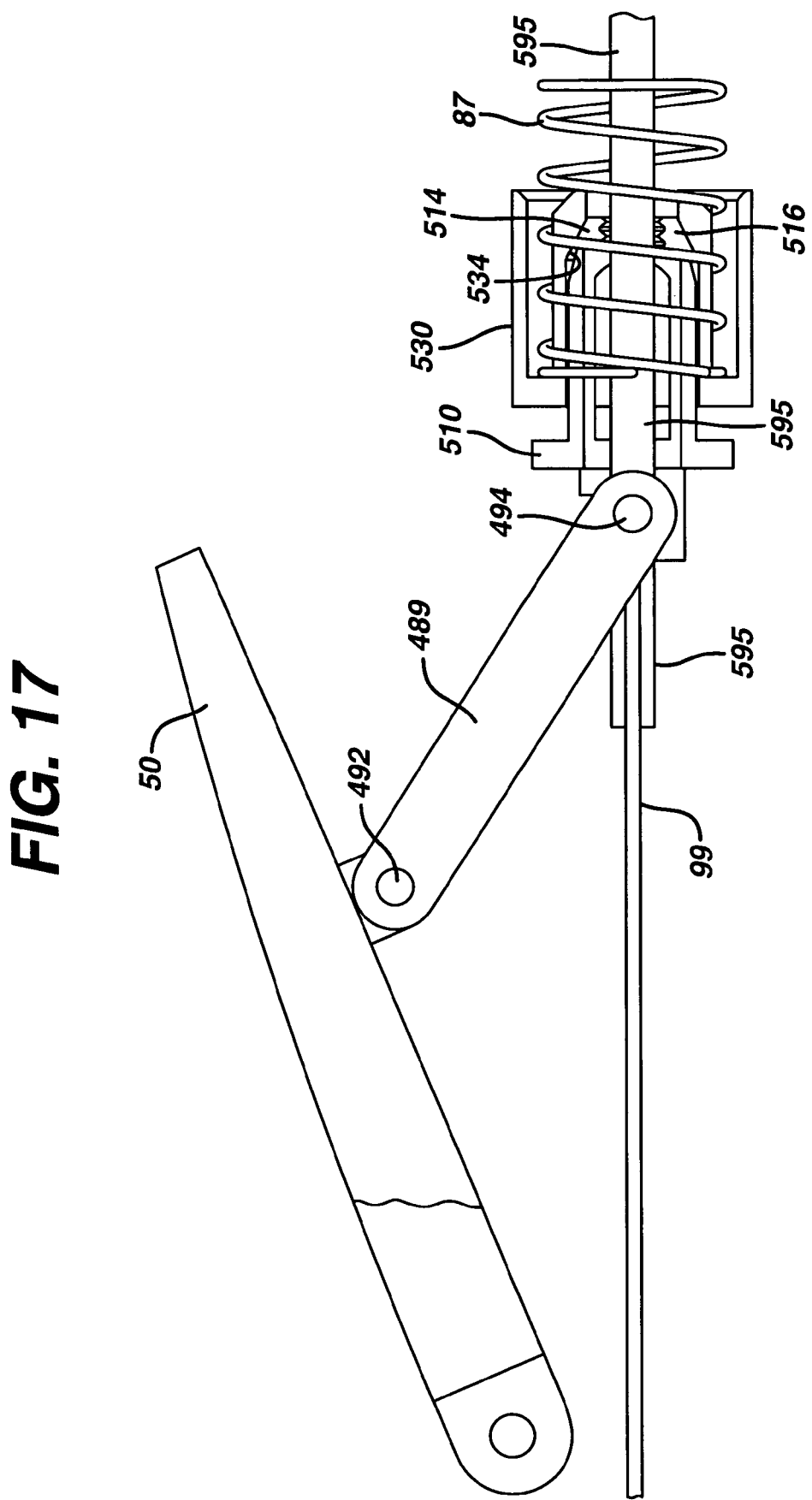
FIG. 17 illustrates a portion of an actuation mechanism in an alternative embodiment of the present invention employing a collet to couple the actuation mechanism to the pulling member.

FIG. 17 illustrates another alternative embodiment for providing coupling and decoupling of the actuation mechanism with the pulling member. The pulling member can include pull wire 99 and sleeve 595 fixed to the proximal end of pull wire 99. Actuator lever 50 is pivotably pinned to link 489 by pin 492. The other end of link 489 is pivotably linked to a collet 510 at pin 494. Sleeve 95 extends through a bore in Collet 510. Collet 510 includes split collet jaws 514 and 516. Collet receiver 530 is supported in housing 47 to move proximally against the biasing force of spring 87. Collet receiver 530 has an inwardly facing conical surface 534. Closing actuator lever 50 causes link 489 to urge collet 510 in a proximal direction along the longitudinal axis of the handle 40, until collet jaws 514 and 516 engage the inclined surface 534 of collet receiver 530. Upon engaging the surface 534, the jaws 514 and 516 are urged radially inwardly to grip the sleeve 595. Further closure of actuator lever 50 causes sleeve 595 and pull wire 99 to move in a proximal direction (to the right in FIG. 17).

The embodiments shown employ partial closing of the lever 50 to provide engagement of the actuation mechanism with the pulling member. Alternatively, a separate actuator, such as a button, switch, or knob could be used to provide engagement of the actuation mechanism with the pulling member.

FIG. 14 is an enlarged view of ratchet mechanism 110 of FIG. 8 in a configuration in which actuator 50 is in the completely closed position. Pawl 36 engages teeth 97 of rack 102 to keep tension on pull cable 99, keeping the end effector closed. To disengage pawl 36, the user depresses release 44. Depressing release 44 causes release arm 49 to slide along leaf spring 85. When release arm 49 passes over dimple 104 on leaf spring 85, leaf spring 85 is deflected downward to disengage pawl 36 from rack 102.

During use, handle 40 may be held in a manner shown in FIG. 4. The steps for use of endoscopic accessory 124 with handle 40 may include placing handle 40 within a hand, gripping flexible shaft 65 between the thumb 120 and another finger on that hand, advancing the device to an area within the body, and actuating the actuator lever 50 between the palm 112 and another finger of that hand without using the thumb 120. This allows single-handed use of accessory 124 while endoscope 128 is actively being held with the other hand. Accessory 124 may be fed into the working channel 133 of endoscope 128 with the thumb and index finger to advance the end effector to the target tissue area.

A set of instructions informing the endoscopist of the steps of use may be packaged with the device. This may be beneficial in teaching and showing the technique that is enabled by use of handle 40. Such an instruction set can include a list of steps with respect to using the handle 40. The instruction set can be associated with a medical device having the handle, such as by direct association wherein the instruction set is provided with the medical device, such as in the form of printed material on a label, a separate insert booklet, brochure, or sheet, recorded on a video, CD or DVD provided with the medical device, or printed directly onto a package containing the medical device. Alternatively, the instruction set can be indirectly associated with the medical device by providing the instruction set separately from the medical device, but with reference to use of the medical device, such as in the form of materials provided on a web site, in a training brochure, video, CD, or DVD.

The handle 40 has been shown as a component of a medical device such as flexible endoscopic accessory 124. If desired, handle 40 can be provided as a stand alone product which is releasably attachable to different flexible shafts 65 so as to be interchangeable with different end effectors. Handle 40 and its associated flexible shaft 65 and end effector can be made for repeated use, or can be disposable and be provided presterilized in a suitable package.

While preferred embodiments of the present invention have been shown and described herein, it will be obvious to those skilled in the art that such embodiments are provided by way of example only. For example, the structures described in relation to the present invention can be equivalently described in terms of a means for accomplishing the function of the structure. While the embodiments disclosed are directed primarily to use with gastroscopes, it will be understood that the invention is also useful with other endoscopic devices, including without limitation laparoscopes. Numerous variations, changes, and substitutions will now occur to those skilled in the art without departing from the invention. Accordingly, it is intended that only the spirit and scope of the appended claims limit the invention.

What is claimed is:

1. A medical device comprising:
a flexible member;
an end effector operatively associated with a distal end of the flexible member; and
an elongate handle extending longitudinally from a handle proximal end to a handle distal end, the handle being operatively associated with the proximal end of the flexible member, wherein the flexible member extends from an end of the elongate handle along an axis generally parallel to a longitudinal axis of the elongate handle;
wherein the handle comprises an actuator operable by the same hand used to grasp the handle for operating the end effector through the flexible member with a portion of the flexible member in a looped configuration behind the back of the same hand;

wherein the actuator is disposed on the handle to be operated by the same hand holding the handle without the use of the thumb or index finger of the same hand, while the thumb and index finger of the same hand are free to grip and advance the portion of the flexible member in a looped configuration;

wherein the handle has an outer surface, the handle outer surface extending lengthwise intermediate the handle proximal and distal ends, with the handle outer surface having a maximum width portion disposed intermediate the handle proximal and distal ends, wherein the handle outer surface has a length that is greater than the width of the maximum width portion, and wherein the actuator comprises a lever, the lever extending lengthwise alongside at least a portion of the handle outer surface, and wherein the lever extends alongside the maximum width portion of the handle outer surface;

the medical device further comprising a ratchet mechanism; and the medical device further comprising a release disposed at a first end of the handle, wherein the elongate flexible member extends from a second, opposite end of the handle; and wherein the release is operable to disengage the ratchet mechanism.

2. The device of claim 1 wherein the end effector is selected from the group consisting of a biopsy forceps, grasping forceps, and surgical scissors.

3. The device of claim 1 wherein the flexible member has a length of at least 0.5 meter.

4. The device of claim 1 wherein the flexible member has a flexible shaft having a length of at least 1.0 meter.

5. The device of claim 1 wherein the lever has a length that is at least half the length of the handle.

6. A system for operating a flexible endoscopic device with one hand comprising:
- an end effector having a first configuration and a second configuration;
- a handle;
- a flexible shaft extending intermediate the end effector and the handle;
- the handle comprising:
  - a housing, the housing being longer than the housing is wide, wherein the flexible shaft extends from the housing along an axis generally aligned with length of the housing;
  - an actuator comprising a lever extending lengthwise alongside the housing and operable by the same hand holding the housing to actuate the end effector from the first configuration to the second configuration; wherein at least the thumb and index finger of the same hand holding the housing are free to grip and release the flexible shaft of the device; and
  - a release operable for returning the end effector to the first configuration.

7. The system of claim 6 wherein the release is disposed at a first end of the handle and wherein the elongate flexible member extends from a second, opposite end of the handle.

8. The system of claim 6 wherein the lever has a length at least half that of the handle.

9. The medical device of 6 further comprising a ratchet operable with the lever.

* * * * *